UNITED STATES PATENT OFFICE.

ABRAM L. BOWER, OF BOYERTOWN, PENNSYLVANIA.

DENTAL PREPARATION FOR CAPPING PULPS.

SPECIFICATION forming part of Reissued Letters Patent No. 12,277, dated October 25, 1904.

Original No. 731,849, dated June 23, 1903. Application for reissue filed April 9, 1904. Serial No. 202,437.

*To all whom it may concern:*

Be it known that I, ABRAM L. BOWER, a citizen of the United States, residing at Boyertown, in the county of Berks and State of Pennsylvania, have invented a new and useful Dental Preparation to be Used in the Operation of Capping Pulps, of which the following is a specification.

My discovery is a combination of thymol and oxid of zinc, which forms a hard and uniform mass which is an ideal combination for capping pulps.

The preferred manner of preparation is as follows: Melt the thymol on the surface of a sheet of glass or on the smooth surface of a flexible material like a sheet of tin or other metal or in a very shallow vessel. Then drop the oxid of zinc into the melted thymol until the latter is nearly taken up by the powder. Then the mixture may be manipulated by stirring, shaking, or otherwise, making a semifluid mass which soon hardens and which may then be cracked or broken into pieces of any desirable size and then stored in stoppered bottles. In hot weather the mixture may be cooled to facilitate the "setting" of the mass. No definite proportions need be observed in compounding these materials except that the quantity of the second ingredient must not be too great.

Before the plastic mass "sets" the precaution should be taken to spread the mass out over the smooth surface, so as to form a cake or layer not more than from one-eighth to one-sixteenth of an inch in thickness.

The manner of using the preparation is as follows: When it is desired to cap a dental pulp or to place a non-conductive lining in the bottom of a dental cavity, the cavity is dried and the points of a pair of pliers are heated in the flame of a spirit-lamp and then touched to a crystal of thymol, which melts and flows up the pliers by capillary attraction. The pliers are permitted to cool until or about the temperature of the body. The proper temperature can be determined by touching the side of the pliers on the back of the hand. Then the pliers are touched to the bottom of the cavity and opened, permitting the thymol to flow over the bottom of the cavity. A piece of the combination of thymol and the second ingredient is then touched to the fluid, causing it to adhere. A ball burnisher is then heated slightly and the preparation is touched with it. It becomes fluid and covers the exposed pulp and immediately hardens. Any excess of the material can then be picked or broken away readily, and a filling can be inserted immediately.

This preparation is very hard and is somewhat brittle. It has decided germicidal and non-conductive properties.

From the foregoing it is to be understood that the essential thought involved in the invention is the production of a cement composed of thymol or an equivalent crystalline substance having a melting-point approximately between 95° and 120° Fahrenheit and oxid of zinc or an equivalent powdered or granular substance of less fusibility.

The various combinations which may be formed have valuable qualities which make them useful not only in dentistry, but in other arts, such as for general cementing purposes in connection with glass, porcelain, and other articles. However, whatever materials are combined, the invention only deals with such combinations as are produced by melting the crystalline part and combining therewith the less fusible part while the former is in a melted condition.

The manner of preparing the various combinations is the same, and the invention has therefore been exemplified herein by a description of producing a cement of thymol and oxid of zinc, because such cement appears to be the most valuable of the group.

Having thus described the invention, what is claimed, and desired to be secured by Letters Patent, is—

1. A composition consisting of a combination of thymol with a metallic compound.

2. A composition consisting of a combination of thymol with a metallic salt.

3. The herein-described combination of thymol with oxid of zinc, substantially as and for the purpose specified.

In testimony whereof I hereunto affix my signature in the presence of two witnesses.

ABRAM L. BOWER. [L. S.]

Witnesses:
LUTHER F. GILBERT,
IRWIN T. EHST.